United States Patent [19]

Kaufman et al.

[11] Patent Number: 5,304,325
[45] Date of Patent: Apr. 19, 1994

[54] EMULSIONS CONTAINING ALKYL- OR ALKYLGLYCEROPHOSPHORYL CHOLINE SURFACTANTS AND METHODS OF USE

[75] Inventors: Robert J. Kaufman; Thomas J. Richard, both of University City, Mo.

[73] Assignee: HemaGen/PFC, St. Louis, Mo.

[21] Appl. No.: 791,420

[22] Filed: Nov. 13, 1991

[51] Int. Cl.$^5$ .................. B01J 13/00; A61K 9/107
[52] U.S. Cl. .................... 252/312; 424/529; 514/832; 514/833; 514/938
[58] Field of Search ............ 252/312; 424/2, 529, 424/532, 78; 623/1, 4; 514/938, 939, 832, 833; 554/80, 82, 84

[56] References Cited

U.S. PATENT DOCUMENTS

| | | | |
|---|---|---|---|
| 3,911,138 | 10/1975 | Clark, Jr. | 424/352 |
| 4,110,474 | 8/1978 | Lagow et al. | 424/350 |
| 4,159,988 | 7/1979 | Eibl et al. | 554/82 X |
| 4,187,252 | 2/1980 | Lagow et al. | 260/653 |
| 4,252,827 | 2/1981 | Yokoyama et al. | 424/366 |
| 4,423,077 | 12/1983 | Sloviter | 424/325 |
| 4,443,480 | 4/1984 | Clark, Jr. | 424/352 |
| 4,534,978 | 9/1985 | Yokoyama et al. | 514/429 |
| 5,061,484 | 10/1991 | Heldebrant | 424/78 |
| 5,085,854 | 2/1992 | Fukuda et al. | 424/63 |
| 5,152,923 | 10/1992 | Weder et al. | 252/312 |

FOREIGN PATENT DOCUMENTS

| | | | |
|---|---|---|---|
| 3943000 | 7/1991 | Fed. Rep. of Germany | 554/82 |
| 59-016495 | 6/1984 | Japan | 554/80 |

*Primary Examiner*—Richard D. Lovering
*Assistant Examiner*—Daniel S. Metzmaier
*Attorney, Agent, or Firm*—Wood, Herron & Evans

[57] ABSTRACT

Oil and water emulsions containing alkylphosphoryl choline or alkylglycerophosphoryl choline surfactants are disclosed. The surfactants have the following general structures:

I.  $\begin{array}{l} CH_2-OR_1 \\ | \\ CH_2-OR_2 \\ | \\ CH_2-PC \end{array}$

II. $R_3-PC$

In the above general structures, $R_1$, $R_2$ or $R_3$ is alkyl, alkenyl, fluoroalkyl and alkenyl; and PC is the phosphoryl choline. The emulsions are useful as oxygen transport agents, artificial bloods or red blood cell substitutes.

17 Claims, No Drawings

EMULSIONS CONTAINING ALKYL- OR ALKYLGLYCEROPHOSPHORYL CHOLINE SURFACTANTS AND METHODS OF USE

TECHNICAL FIELD OF THE INVENTION

This invention relates to emulsions of oil and water and processes of making and using them. More particularly, this invention relates to novel emulsions that contain an oil (using this term in a general sense), water and a novel surfactant that may be generally identified as an alkylphosphoryl choline or an alkylglycerophosphoryl choline. Such emulsions have general utility for many industrial uses and are especially useful as oxygen transport agents, artificial bloods or red blood cell substitutes and as contrast agents for biological imaging.

BACKGROUND OF THE INVENTION

Emulsions permit extensive subdivision of an oil (using this term in a general sense) with a consequent formation of an enormous oil-water interface. Emulsions may be of the oil-in-water type or water-in-oil type and may involve other phases and interfaces. Where these dispersions are of the oil-in-water type, they are usually referred to as oil emulsions or soluble oil compositions. Where the phases are reversed as in a water-in-oil type, they are commonly referred to as inverted emulsions. There are many industrial uses of oil and water emulsions including paints, adhesives, lubricants, cleansing agents, soaps, insecticides, cosmetics, pharmaceuticals and therapeutic agents. This short list is only the beginning of a vast number of uses for oil and water emulsions.

One class of emulsions that has developed over a number of years is fluorocarbon emulsions as oxygen transport agents or artificial bloods. U.S. Pat. No. 3,911,138 which issued to Clark is an early example from the patent art which discloses perfluorocarbon emulsions as artificial bloods. As developed in this patent, neat fluorocarbon liquids cannot be injected into the blood stream, because their hydrophobic character makes them immiscible in the blood and, as a result, when they are transported in small blood vessels, they may cause vascular obstruction and death. As a consequence, for medical uses that require intravascular injection, highly fluorinated organic compounds or fluorochemicals must be dispersed as physiologically acceptable emulsions as developed in the above Clark patent and U.S. Pats. Nos. 4,110,474; 4,187,252 and 4,443,480.

There have been various attempts to make emulsions that are both stable and incorporate relatively large amounts of fluorocarbons that are required in clinical practice where the total volume of the emulsion that can be administered is limited, e.g., as in artificial bloods. An objective in the preparation of such emulsions is the employment of an acceptable fluorocarbon that may be excreted from the body within a clinically acceptable time period. Furthermore, compositions are required that are sterilizable without destruction of their stability.

A fluorocarbon emulsion that has been approved by the FDA is FLUOSOL DA which is an emulsion of perfluorodecalin and perfluorotripropylamine in a mixture of two surfactants, namely, egg yolk phospholipid and Pluronic F-68. This product, however, is not stable in the liquid state and must be stored frozen. Furthermore, the required presence of the perfluorotripropylamine in this emulsion to help stabilize it disadvantages the emulsion's medical usefulness because the half life of the perfluorotripropylamine in the liver and other body tissues is longer than desirable (see K. Yokoyama et al, "A Perfluorochemical Emulsion as an Oxygen Carrier" *Artif. Organs (Cleve)*, 8 (1) pp. 34–40 (1984)). Finally, this emulsion contains only about 12% fluorocarbon by volume and thus it is much less therapeutically effective than desired because of its low oxygen content capacity.

Various surfactants have also been investigated in an attempt to produce useful and stable emulsions of fluorocarbons as oxygen transport agents in artificial bloods. For example, fluorocarbon emulsions containing a hydrogenated phospholipid, a nonionic polymeric surfactant and a surfactant selected from C6-22 fatty acids, their salts and monoglycerides, must also be stored at 4° C. See, e.g., Japanese Pat. Appln. 59-067,229; U.S. Pat. No. 4,252,827 and German Offen. DE 2630506.

European Pat. Appln. 87300454.3 of Clark and Shaw describes novel emulsions of highly fluorinated organic compounds for use as oxygen transport agents and artificial bloods. This Clark and Shaw application discloses emulsions that are stable even when they contain higher levels of perfluorocarbons of up to about 75% by volume. The fluorocarbons of these emulsions display acceptable rapid excretion times from the liver and other body tissues, as well as being easily sterilized. These emulsions contain an oil as an emulsifying adjuvant in a composition containing the fluorochemical, surfactant and water. While improvements disclosed in this Clark and Shaw application are significant and alleviate many of the difficulties in the long search for effective transport agents in artificial bloods, there is a continuing need for further development.

In brief, emulsions of the oil and water type provide a very important role in many industries and numerous patents have been granted covering them. Research continues with efforts toward developing new emulsifying agents that provide emulsions having greater stability and broader utility in many industries including medical and non-medical fields.

SUMMARY OF THE INVENTION

This invention is directed to emulsions of the oil and water type. According to this invention, novel surfactants have been found to form surprisingly stable oil-in-water emulsions. More particularly, fluorochemical (hereinafter sometimes simply "PFC") emulsions have been made and found to significantly increase the circulatory blood residence time of the PFC and favorably alter the tissue distribution of the PFC in critical organs, such as the liver and spleen. Furthermore, the novel surfactants of this invention have been found to significantly ameliorate the adverse drop in hematocrit, or red blood cell count, after intravenous infusion, normally associated with most lecithin based PFC emulsions.

The emulsions of this invention contain alkylphosphoryl choline or alkylglycerophosphoryl choline surfactants. These surfactants have the following general structures:

I.  $CH_2-OR_1$
    $CH-OR_2$
    $CH_2-PC$

II. $R_3-PC$

More specifically, $R_1$, $R_2$ or $R_3$ is alkyl, alkenyl, fluoroalkyl and alkenyl. Each group may contain about 6 to about 54 carbon atoms, may be saturated or unsaturated, and may be a straight chain aliphatic group or branched aliphatic group. $C_{12}$–$C_{18}$ carbon atoms are presently preferred for the $R_1$ and $R_2$ groups of general structure I, and $C_6$–$C_{32}$ carbon atoms for $R_3$, when employed as surfactants for medical PFC emulsions of this invention. Most preferably, $R_1$ and $R_2$ are a $C_{14}$–$C_{18}$ saturated or unsaturated aliphatic group. In general, these R groups are the residues of aliphatic alcohol or halide reactants when synthesized by methods of this invention.

PC in the above structures is the phosphoryl choline group:

$$-O-\overset{O}{\underset{O}{P}}-OCH_2CH_2N^+(R_4)_3$$

where $R_4$ is hydrogen or lower alkyl such as methyl, ethyl and propyl. The hydrogen or methyl group is preferred in medical PFC emulsions of this invention.

This invention also includes methods of making these surfactants, emulsions containing them and methods of using them as oxygen transport agents, artificial bloods or red blood cell substitutes. Other objectives of this invention and advantages will become apparent from the following detailed description.

DETAILED DESCRIPTION

The emulsions of this invention comprise an oil, water and a surfactant of the above identified type. In general, the oil may be contained in amounts of from about 1 to 90% by total volume of the water and oil. More specifically, for instance, in medical applications for intravenous use, about 60% v/v (115 w/v %) is a practical limit because of viscosity limitations for an intravenous product. Higher amounts may be employed for other applications. The surfactant may be contained in amounts from about 0.5 to about 10% by weight, usually about 1–2% by weight of the emulsion. These components are identified with greater particularity as follows.

A. Oil

The term "oil" is used herein in a general sense to identify a large class of substances whether of mineral, vegetable, animal, essential, synthetic or edible origin. Thus, the term "oil" is used herein as applied to a wide range of substances that are quite different in chemical nature. In the classification of oils by type or function, for example mineral oil is derived from petroleum and includes aliphatic or wax-based hydrocarbons, aromatic or asphalt-based hydrocarbons or mixed aliphatic and aromatic based hydrocarbons. Also included in the mineral classification are petroleum-derived oils such as refined paraffin oil, and the like. In the vegetable classification, oils are chiefly derived from seeds or nuts and include drying oils such as linseed and tongue oil; semi-drying such as safflower and soy bean oils; nondrying such as castor, cottonseed and coconut oils and inedible soap stocks such as palm and coconut oils. In the animal classification, oils usually occur as fats in tallow, lard and stearic acid sources. The liquid animal types include fish oils, oleic acid, sperm oil, etc. and they usually have a high fatty acid content. In the essential oil classification, complex volatile liquids may be derived from flowers, stems and leaves, and often the entire plant. These essential oils include turpenes such as pinene, dipentene, etc. and are chiefly used for perfumery and flavorings. In the edible classification, included are some vegetable oils, such as olive, cottonseed, corn and peanut, as well as some special fish oils such as cod-liver, haliver, shark liver, and so forth which are used largely as medicines for their high vitamin content. Included in this wide range of substances that may be classified as oils for purposes of this description are those synthesized organic compounds that are oleophilic such as the highly fluorinated organic compounds or perfluorocompounds that are capable of being synthesized by well known chemical or electrochemical processes.

In this description, "fluorochemical" or "PFC" is used to describe either a highly fluorinated organic compound of perfluorocarbon or fluorinated chemical. Further, these terms are used interchangeably. The term "perfluorocarbon" includes a "cyclic" or "acyclic" compound of carbon. Substituted derivatives thereof are also included where fluorocarbons have other elements within their structures such as oxygen, nitrogen and bromine, etc. It should also be noted that the term "perfluorocarbon" denotes substitution of all hydrogen atoms attached to the carbon atom chain or ring and any carbon side groups with fluorine. However, "fluorocarbon" is meant to include partially or substantially fluorinated fluorinated compounds. This is permissible providing that the lack of complete replacement of all hydrogens does not affect the essential non-toxic characteristics of the preferred medical fluorocarbons of this invention. Among the perfluorocarbon compounds which may be employed are perfluorotributylamine (FC47), perfluorodecalin (PP5), perfluoromethyldecalin (PP9), perfluorooctylbromide, perfluorotetrahydrofuran (FC80), perfluoroether (PID) $[(CF_3)_2CFOCF_2(CF_2)_2CF_2OCF(CF_3)_2]$, perfluoroether (PIID)$[(CF_3)_2CFOCF_2(CF_2)_6CF_2OCF(CF_3)_2]$, perfluoropolymer (E3) $[CF_3CHF(OCF_2\overset{CF_3}{\underset{|}{CF}})_2OCF_2CF_2CF_3]$, perfluoropolymer (E4) $[CF_3CHF(OCF_2\overset{CF_3}{\underset{|}{CF}})_3OCF_2CF_2CF_3]$, perfluoroetherpolymer (Fomblin Y/01), perfluorododecane, perfluorobicyclo[4.3.0]nonane, perfluorotrimethylcyclohexane, perfluorotripropylamine, perfluoroisopropylcyclohexane, perfluoroendotetrahydrodicyclopentadiene, perfluoroadamantane, perfluoro-exo-tetrahydrodicyclopentadiene, perfluorobicyclo[5.3.0.]decane, perfluorotetramethylcyclohexane, perfluoro-1-methyl-4-isopropylcyclohexane, perfluoron-butylcyclohexane, perfluorodimethylbicyclo[3.3.1.]-nonane, perfluoro-1-methyl adamantane, perfluoro-1-methyl-4-t- butylcyclohexane, perfluorodecahydroacenaphthene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo[4.3.0.] nonane, perfluoro-p-diisopropylcyclohexane, and perfluoro-m-diisopropylcyclohexane. Chlorinated perfluorocarbons, such as chloroadamantane and chloromethyladamantane as described in U.S. Pat. No. 4,686,024 may be used. Such compounds are described, for example, in U.S. Pats. Nos. 3,962,439; 3,493,581; 4,110,474; 4,186,253; 4,187,252; 4,252,827; 4,423,077; 4,443,480; 4,534,978 and 4,542,147, European Pat. Applns. Nos. 80710 and 158,996, British Pat. Specification 1,549,038 and German Offen. 2,650,586. Of course, it should be understood that mixtures of any of these highly fluorinated organic compounds may also be used in the emulsions and processes of this invention.

B. surfactant

According to this invention, novel surfactants have been found to form surprisingly stable oil-in-water emulsions. More particularly, stable PFC emulsions have been made and found to significantly increase the circulatory blood residence time of the PFC and favorably alter the tissue distribution of the PFC in critical organs, such as the liver and spleen. Furthermore, surfactants of this invention have been found to significantly ameliorate the adverse drop in hematocrit, or red blood cell count, after intravenous infusion, normally associated with most lecithin based PFC emulsions.

The emulsions of this invention contain alkylphosphoryl choline or alkylglycerophosphoryl choline surfactants. These surfactants have the following general structures:

I. 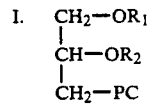

II. $R_3$—PC

More specifically, $R_1$, $R_2$ or $R_3$ is alkyl, alkenyl, fluoroalkyl and alkenyl. Each group may contain about 6 to about 54 carbon atoms, and may be a straight chain aliphatic group or branched aliphatic group. $C_{12}$–$C_{18}$ carbon atoms are presently preferred for the $R_1$ and $R_2$ groups of general structure I, and $C_6$–$C_{32}$ carbon atoms for $R_3$, when employed as surfactants for medical PFC emulsions of this invention. Most preferably, $R_1$ and $R_2$ are a $C_{14}$–$C_{18}$ saturated or unsaturated aliphatic group. In general, these R groups are the residues of aliphatic alcohol or halide reactants when synthesized by methods of this invention.

PC in the above structures is the phosphoryl choline group:

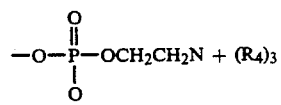

where $R_4$ is hydrogen or lower alkyl such as methyl, ethyl and propyl. The hydrogen or methyl group is preferred in medical PFC emulsions of this invention.

Examples of aliphatic alcohol or halide reactants to form the $R_1$, $R_2$ or $R_3$ groups in the above structures are tetradecylbromide, oleyl alcohol, hexadecylbromide, octadecyl alcohol, 1H,1H,7H-dodecafluoro-1-heptanol, 2-Iodo-1,1,1-trifluoroethane, 1H,1H,11H-eicosafluoroundecan-1-ol., 1-Iodo-1H-1H-perfluorobutane, 1-Iodo-1H,1H,2H,2H-perfluorodecane, 1-Iodo-1H,1H,2H,2H-perfluorododecane, 1-Iodo-1H,1H,2H,2H-perfluorooctane, 4-Iodo-2-trifluoromethyl-1-1,1,1,2-tetrafluorobutane, 2,2,3,3,4,4,5,5-octafluorohexan-1,6-diol, 1-Iodo-1H,1H-pentadecafluorooctanol-1, 3,3,4,4,4,-pentfluorobutanol-2, (1H,1H-pentafluoropropanol-1), and (Perfluoro-tert-butanol). In addition, Atochem, Dupont, 3M and Hoechst all market suitable mixtures of the formula $R_f$—$CH_2$—$CH_2$—X (X=OH,I) in which $R_f$ is comprised of varying mixtures of $C_nF_{2n+1}$ perfluoroalkyl linear and branched chains. Typically, the mixture's "n" value is either 1-3, 4-8, or 6-12. These same companies sell $R_f$—COOH, and it is a trivial matter to reduce the carboxylate in these compounds to produce $R_fCH_2OH$. Also marketed are perfluoroalkenes of many types (which could easily serve as substrates for the addition of ROH) and oxiranes (the oxirane ring is hydrogen containing, with the rest of the molecule being perfluorochemical in nature). The oxirane, too, is easily opened nucleophilically by ROH.

Specific examples of surfactants under the general structures are 1,2-dioctylglycero-3-phosphoryl choline, 1,2-ditetradecylglycero-3-phosphoryl choline, 1,2-dihexadecylglycero-3-phosphoryl choline, 1,2-dioctadecylglycero-3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1-2-dioctadecylglycero-3-phosphoryl choline, 1-octadecyl-2-hexadecylglycero-3-phosphoryl choline, 1-tetradecyl-2-hexadecylglycero-3-phosphoryl choline, 2,2-ditetradecyl-1-phosphoryl choline ethane and 1-hexadecyl-tetradecylglycero-3-phosphoryl choline and mixtures of these novel surfactants with other known surfactants may be employed as described hereinafter.

C. Emulsion Characteristics

The emulsions of this invention are made by dispersing oil in water in the presence of the above identified surfactants. The surfactant enhances the dispersion and stabilization of the liquid phases. While dispersions may be generally referred to herein as emulsions, it should be understood that they may be considered solutions, micellar solutions, microemulsions, vesicular suspensions, or mixtures of all of these physical states. Accordingly, the term "emulsion" as used herein covers all these states and the novel surfactant or solubilizing agent is employed to enhance stable mixtures of these physical states of the oil and water phases. For example, where a fluorochemical oil is emulsified in water, another oil may serve as an emulsifying adjuvant as described in the aforementioned Clark and Shaw European Pat. Appln. 87300454.3. We wish to emphasize that, according to this invention, this emulsifying adjuvant is optional. Successful emulsions have been prepared with no such adjuvant. When an adjuvant is employed, a liquid fatty oil such as a mono-, di-, or triglyceride or mixtures thereof are the preferred agents. Where such oil and and oleophilic PFC combinations are emulsified in water, as provided hereinafter, complex phases and interfaces may form.

Preferably, for artificial blood, the emulsions of this invention contain a PFC or mixture of PFCs, and most preferably contain a fluorocarbon selected from the group consisting of perfluorodecalin, perfluoromethyldecalin, perfluorodimethyladamantane, perfluorooctylbromide, perfluoro-4-methyloctahydroquinolidizine, perfluoro-N-methyl-decahydroquinoline, F-methyl-1-oxa-decalin, perfluorobicyclo(5.3.0) decane, perfluorooctahydroquinolidizine, perfluoro-5,6-dihydro-5-decene and perfluoro-4,5-dihydro-4-octene. For use as a contrast agent for biological imaging perfluorooctylbromide is one of the preferred PFCs according to this invention.

While the PFCs or mixture of PFCs may comprise 10% up to about 75% by volume, or more, of the emulsions, preferably they comprise at least 40% by volume. When the emulsions are to be used as "artificial bloods" or red blood cell substitutes, the PFC is present in as high a volume concentration as possible, e.g., 40% by volume is often preferred because that concentration matches the approximate oxygen content capacity of whole blood.

In a broader sense, as indicated above, the amount of oil in the emulsions may vary over a wide range of concentrations from about 0.5 to about 90% by volume, or more. It depends on the concentration and properties of the other components of the emulsion and its use. For example, when used as an artificial blood, PFC oil is present in an acceptable amount along with other oil emulsifying adjuvant. The actual oil concentration to produce an acceptable emulsion for any given set of components is determined by preparing and testing the stabilities of emulsions at various oil concentrations. Within this teaching for PFC artificial bloods, for instance, between 0 and 30% by weight oil adjuvant and 10–70% by volume PFC oil are used.

The amount of a particular surfactant used in the emulsions of this invention depends upon the amounts and properties of other components of the emulsion as indicated above. Generally about 0.5–10% by weight of surfactant, preferably, about 1–2% by weight is used. The surfactant of this invention may be used with other surfactants as indicated above. Among other surfactants useful in the emulsions of this invention are any of the known anionic, cationic, non-ionic and zwitter-ionic surfactants. These include, for example, anionic surfactants, such as alkyl or aryl sulfates, sulfonates, carboxylates or phosphates, cationic surfactants such as mono-, di-, tri- and tetraalkyl or aryl ammonium salts, non-ionic surfactants, such as alkyl or aryl compounds, whose hydrophilic part consists of polyoxyethylene chains, sugar molecules, polyalcohol derivatives or other hydrophilic groups and zwitter-ionic surfactants that may be combination so the above anionic or cationic groups, and whose hydrophobic part consists of any other polymer, such as polyisobutylene or polypropylene oxides.

When the emulsions of this invention are to be used in artificial bloods or red blood cell substitutes, the surfactant, or combinations of them, must be physiologically acceptable. For example, in artificial bloods an alkylphosphoryl choline or dialkylglycerophosphoryl choline is used where the alkyl group is about $C_{12}$–$C_{18}$ as exemplified by 1-octadecyl-2-hexadecylglycero-3-phosphoryl choline.

The emulsions may be prepared using any order of mixing the main components of oil, surfactant and water. However, for optimal PFC emulsions the PFC is first mixed with the adjuvant oil in the presence of a combination of all or part of the surfactant and some water. Then the final emulsion is prepared by emulsifying this first emulsion in the remaining water and any remaining surfactant as described in the above Clark and Shaw European Appln. 87300454.3 which is incorporated herein by reference.

The mixing and emulsification of components may be done using any of the conventional mixers and emulsifiers. For example, Fisher brand touch mixers, Microfluidizers, Gaulin and Rannie Homogenizers may be employed.

The following non-limiting examples illustrate various embodiments of this invention.

DETAILED EXAMPLES

Surfactant Synthesis

The surfactants of this invention were synthesized from the corresponding dialkylglycerols and the synthetic sequences are represented by the following schemes or methods.

Scheme I - Preparation of symmetrical dialkyletherglycerols:

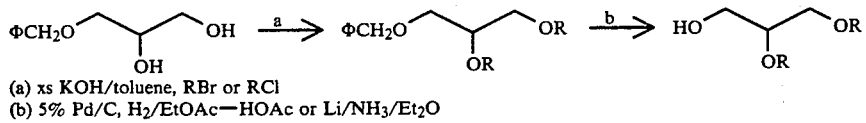

(a) xs KOH/toluene, RBr or RCl
(b) 5% Pd/C, H₂/EtOAc—HOAc or Li/NH₃/Et₂O

Scheme II - Preparation of unsymmetrical dialkyletherglycerols:

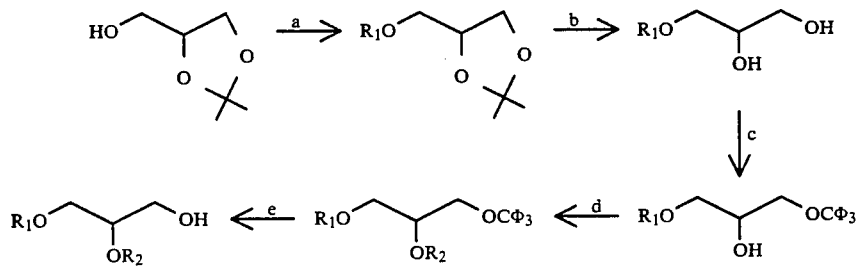

(a) xs KOH/toluene, RBr or RCl
(b) H₂SO₄/H2O/MeOH
(c) φ₃CCl
(d) identical to a
(e) HCl(anhyd)/pet ether

Method A: Preparation of dialkylglycerophosphoryl choline

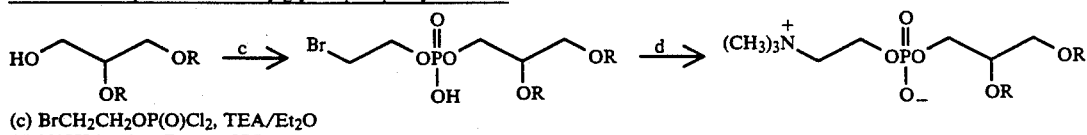

(c) BrCH₂CH₂OP(O)Cl₂, TEA/Et₂O
(d) N(CH₃)₃, then Dowex SBR

Method B: Preparation of dialkylglycerophosphoryl choline

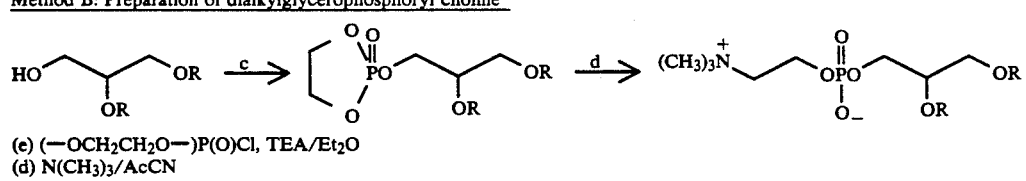

(e) (—OCH₂CH₂O—)P(O)Cl, TEA/Et₂O
(d) N(CH₃)₃/AcCN

In connection with the above schemes and methods, the term "symmetrical" is employed to designate dialkyl compounds where both alkyl groups are identical and "unsymmetrical" where the alkyl groups differ. Employing the schemes and methods, the following illustrate specific examples of making dialkyletherglycerols as precursers of the dialkylglycerophosphoryl choline surfactants of this invention.

3-Benzyl-1,2-dihexadecylglycerol (Scheme Ia)

To a refluxing mixture of benzylglycerol (50 g, 0.27 mol) and KOH (40 g, 0.76 mol), which had been freshly powdered in an electric milling device, in toluene (500 mL) was added 1-bromohexadecane (252 g, 9.76 mol) over a period of one hour. The mixture was refluxed overnight, with Dean-Stark removal of water of reaction. The slurry was stripped of toluene on a rotary evaporator, then the residue was slurried in CHCl3 and washed with water. The organic phase was dried (MgSO4) and stripped. Unreacted starting material was removed by Kugelrohr distillation (150°, 1 mm Hg). The pot residue was a yellow solid of sufficient purity for use in the next step.

1,2-Dihexadecylglycerol (Scheme Ib)

The residue from the Kugelrohr distillation was transferred to a Parr hydrogenator and dissolved in EtOAc (200 ml) and HOAc (200 ml). Under nitrogen, 5% Pd/C (8 g) was added. Debenzylation was carried out at 50° C. and 50 psig until hydrogen uptake had ceased. The reaction mass was filtered warm and the filter cake washed with chloroform. After evaporation of the volatile components on a rotary evaporator the residue was recrystallyzed from ethyl acetate to yield white crystals (200 g, 69%) m.p. 56°-7° C.

Other compounds prepared by Scheme I 1,2-dioctadecylglycerol*
*This compound may also be named 2,3-bis(octadecyloxy)-1-propanol and this nomenclature may apply to the other compounds.
1,2-ditetradecylglycerol
1,2-dioctylglycerol
1,2-didecylglycerol

2-Bromoethylphosphoryl dichloride

To a mixture of freshly distilled phosphorus oxychloride (62 ml) in 50 ml carbon tetrachloride was added 62 g of bromoethanol, dropwise with stirring at 20° C. The mixture was allowed to stand over night and then heated at reflux for 2 hours to drive off hydrogen chloride. After stripping the carbon tetrachloride the residue was fractionated in vacuo. Yield 70-77 g, b.p. 110°-115° C. @ 12 mm Hg.

2-Bromoethylester of 1,2-dihexadecylglycerol phosphoric acid (Method Ac)

2-bromoethylphosphoryl dichloride (14.5 g, 0.074 ml) was dissolved in anhydrous ether (300 ml) and triethylamine (7.5 g, 0.074 mol). To this solution was added (20 g, 0.037 mol) of dihexadecylglycerol at once at room temperature. The reaction mixture was allowed to stir over night. Hydrolysis of the intermediate was carried out by vigorous stirring with H20 (300 ml) and MeOH (100 ml) for 5 hours. The layers were allowed to separate and the ether layer was dried over MgSO4. After removing the ether on a rotary evaporator 26.3 g of white waxy solid was obtained.

1,2-Dihexadecylglycerophosphoryl choline (Method A)

To a solution of the above 2-bromoethylester of Method A (82 g, 0.18 mol) in methyl ethyl ketone (400 ml) was added trimethylamine (35 g, 0.6 mol) in a sealed vessel, which was then heated to 55° C. for 18 hours. The slurry was then cooled to room temperature, filtered and the cake washed with acetone. The cake was dissolved in hot 90% ethanol (1400 ml), Dowex SBR (200 g) ion exchange resin was added and the slurry stirred for 15 minutes. The resin was filtered off and ethanol-water removed on a rotary evaporator. The residue was dried over P2O5 and then purified by column chromatography to give 35.5 g (42.2% yield) of pure product.

1,2-Dioleylglycerophosphoryl choline (Method B)

To a thoroughly dried 500 ml round bottom flask equipped with condenser, stirrer, and thermometer, was added dioleyl glycerol (Scheme 1b hereinafter) (40 g, 67 mmol) and anhydrous diethyl ether (380 ml). The solids were dissolved by mild warming, then the solution was cooled to room temperature. A solution of 2-chloro-2-oxo-1,3,2-dioxaphospholane (9.8 g, 69 mmol) in diethyl ether (50 ml) was added dropwise, over the space of 15 minutes. At that point, triethylamine (TEA) (7.2 g, 71 mmol) was added, and a white precipitate formed almost immediately. The mixture was stirred for one hour, then filtered under a stream of dry nitrogen. The filtrate was rotary evaporated to obtain a white solid. This solid was dissolved in acetonitrile (400 ml) in a 500 ml serum bottle, and trimethylamine (TMA) (28.0 g, 237 mmol) was added. The bottle was sealed and kept at 65°

C. for 18 hours. After cooling to room temperature, the contents were dissolved in CHC13 and the solvents were evaporated to yield a white solid, which was chromatographed on silica gel (75% CHC13, 22% H20, 3% H20 eluent) to yield the desired product (21.2 g, 41.5% from the starting dioleylglycerol). (Note: Method B was the method of choice for incorporating the phosphoryl headgroup.)

1,2-Dioleylglycerol (Scheme Ib)

A 250 ml flask equipped with a dry ice condenser and a dry ice-acetone bath was charged with anhydrous NH3 (140 ml). After cooling to −65° C. under N2 Li wire (1.35 g) was added in small pieces. Dioleylbenzylglycerol (10 g, .0146 mol) in THF (60 ml) and EtOH (12 g) was added over 30 minutes and then stirred at −65° C. for 15 minutes. The dry ice bath was removed and the reaction mass allowed to warm to room temperature, with evaporation of NH3. Water (100 ml) and heptane (150 ml) were added. The organic phase was washed with water, dried (MgSO4) and stripped of solvent yielding a light yellow oil (7.8 g, 90%).

1-hexadecyl-2-tetradecyl glycerol (Scheme II c, d, e)

1-hexadecyl glycerol (105 g, .33mol) and 93 g (0.33 mol) tritylchloride were dissolved in 300 ml of pyridine. The mixture was heated at 100° C. for 16 hours. After cooling to room temperature 1500 ml of ethyl ether was added and the slurry washed 3 times with cold .5N H2SO4, 5% sodium bicarbonate and 2 times with water. The organic phase was dried over MgSO4, the ether removed on a rotary evaporator and the residue recrystallized from ethanol, yielding the intermediate 1-hexadecyl-3-trityl glycerol (129 g, 70%). The 2 position of this intermediate was alkylated with tetradecyl bromide in the same manner (powdered KOH in toluene) as described earlier for the dialkylation of benzyl glycerol in the preparation of 1,2-dihexadecyl glycerol. The resulting 1-hexadecyl-2-tetradecyl-3-trityl glycerol (128 g) was dissolved in 300 ml of petroleum ether. At room temperature 30 g of anhydrous hydrogen chloride was added. A precipitate formed within a short time. The slurry was stirred at room temperature for 4 hours and then filtered. The solids were recrystallized from acetone (10° C.) to give 45.6 g of product, m.p. 42°-3° C.

Hemolysis Screening of Surfactants

Surfactant Examples 1a–1k according to general Structure I above, and 2a of Structure II above, were prepared following the above procedures. Hemolysis screening of these surfactants is reported in the following Table I.

Surfactants were screened initially by preparing 5% solutions/dispersions of the surfactant in 0.9% saline and admixing 1:1 with rat whole blood. Centrifugation (6 minutes) at 2400 rpm afforded packed cells and a supernate. The surfactant was judged to be hemolytic at the given concentration if the supernate from the centrifugation showed a visually distinct red hue relative to control rat blood. The discoloration of the supernate was not quantified colorimetrically. In the preliminary studies, low molecular weight surfactants 1a and 1b were found to be hemolytic upon mixing with whole red blood and were not subjected to further toxicity testing, thus "N/A" was used in Table I. Those compounds that were found to be non-hemolytic were then tested in a preliminary acute toxicity screen by injection of 40 cc/Kg of a 5% sonicated dispersion of the compound in 0.9% saline into two Sprague Dawley rats. The emulsion passed toxicity testing if the animals survived for 14 days, and these results are reported in Table I. While the study tended to demonstrate that the low molecular weight compounds were hemolytic and therefore toxic, whereas larger $C_{14}$–$C_{18}$ groups were nonhemolytic, further testing may be required to rationalize differences in lethality.

TABLE I

HEMOLYSIS SCREENING OR SURFACTANTS

| Cpd | $R_1$ | $R_2$ | $R_3$ | Hemolytic | Survival at 40 cc/Kg of 5% solution |
|---|---|---|---|---|---|
| 1a | $C_8H_{17}$ | $C_8H_{17}$ | | Yes | N/A |
| 1b | $C_{14}H_{29}$ | $C_{14}H_{29}$ | | Yes | N/A |
| 1c | $C_{16}H_{33}$ | $C_{16}H_{33}$ | | No | 2/2 |
| 1d | $C_{18}H_{37}$ | $C_{18}H_{37}$ | | No | insoluble cpd |
| 1e | $C_{16}H_{33}$ | $C_{14}H_{29}$ | | No | 0/2 |
| 1f | $C_{18}H_{37}$ | $C_{14}H_{29}$ | | No | 2/2 |
| 1g | $C_{14}H_{29}$ | $C_{18}H_{37}$ | | No | 0/2 |
| 1h | $C_{16}H_{33}$ | $C_{18}H_{37}$ | | No | 0/2 |
| 1i | $C_{18}H_{35}$ | $C_{18}H_{35}$ | | No | 2/2 |
| 1j | $C_{18}H_{37}$ | $C_{16}H_{33}$ | | N/A | N/A |
| 1k | $C_{14}H_{29}$ | $C_{16}H_{33}$ | | N/A | N/A |
| 2a | | | $C_{32}H_{65}$ | No | 2/2 |

PERFLUOROCARBON EMULSIONS AND THEIR PROPERTIES

The surfactants of Table I were used to make 40 volume % (v/v) perfluorochemical emulsions. In the above described European Pat. Appln. 87300454.3, it was reported that certain oils, i.e., triglycerides of fatty acids as co-additives greatly improved the stability of lecithin containing emulsions. Therefore, those perfluorochemical emulsions were used as a control for comparison with the perfluorochemical emulsions of this invention. The control emulsion was a 40 v/v % perfluorooctyl bromide emulsion prepared according to the technique of the mentioned European patent application and containing 1.75 w/v % egg yolk lecithin as the surfactant and 2 w/v % safflower oil. The surfactants of the invention were substituted for lecithin and the results of the emulsion's properties are reported in Table II. In Table II, the emulsion compositions, mean particle size as measured by laser light scattering, and stability toward storage in a 5% solution of Serum Albumin in Lactated Ringer's solution after 4 days at 37° C. are reported. All data is for emulsions sterilized for 15 minutes at 121° C. in a rotating basket autoclave, the industry standard for large volume parenterals.

TABLE II

EMULSIONS AND PROPERTIES

| Cpd. | w/v % Cpd. | w/v % Oil | Mean Particle Size (nM) | 4 days Serum (nM) |
|---|---|---|---|---|
| 1a | 2.0 | 0.0 | 235 | 249 |
| 1c | 4.0 | 0.0 | 212 | — |
|    | 1.5 | 2.0 | 270 | 267 |
| 1e | 1.5 | 2.0 | 347 | 385 |
| 1f | 2.0 | 2.0 | 359 | 357 |
| 1g | 2.0 | 2.0 | 392 | 438 |
| 1h | 2.0 | 2.0 | 235 | 9 |
| 1i | 1.8 | 2.0 | 304 | 258 |
| 2a | 1.8 | 2.0 | 275 | 254 |
| Control | 1.75 | 2.0 | 250 | 260 |

For comparison with the data of Table II, the study was repeated with a constant loading of 2 w/v % surfactant, and 2 w/v % safflower oil adjuvant for the control and surfactants of this invention.

TABLE III
EMULSIONS AND PROPERTIES

| Cpd | Mean Particle Size (nM) | 4 days Serum (nM) |
|---|---|---|
| 1c | 421 | 318 |
| 1e | 256 | 256 |
| 1f | 333 | 320 |
| 1g | 207 | N/A |
| 1h | 354 | 460 |
| 1i | 323 | 301 |
| 1j | 229 | N/A |
| 1k | 227 | N/A |
| Control | 226 | 232 |

With reference to the data of Tables I and II, the emulsions displayed very good particle size distribution characteristics as measured by a laser light scatterer, both at the time of preparation ("Mean Particle Size" column) and after 4 days storage at 37° C. in a mixture of Human Serum Albumin and Lactated Ringer's Solution ("Serum" column) designed to mimic blood and plasma. All data point to surprisingly stable emulsions when the surfactants of this invention were substituted for egg yolk lecithin.

IMPACT OF FORMULATION ON PERFLUOROCHEMICAL CIRCULATORY BLOOD RESIDENCE TIME

The emulsions of Tables II and III were studied in a randomized, ten animal per emulsion experiment in which each animal was infused with 20 cc/Kg of emulsion and sacrificed at 48 hours to determine the circulatory perfluorochemical or perfluorocarbon content called "fluorocrit" and abbreviated "Fct". The Fct represents that percentage of the blood that is perfluorocarbon in v/v %.

Two sets of ten rats each were treated with a control emulsion and an emulsion prepared from the surfactant of this invention using a randomized administration design. After 48 hrs., the animals were anesthetized, the chest cavity was opened, and a blood sample (1–2 ml) was withdrawn from the still beating heart. Three to 4 drops of the sample were added to each of three previously tared 4 ml vials containing 10%KOH/EtOH (1.0 ml). The vials were weighed to determine the amount of blood added, then reweighed after an internal standard mixture of 1% octane in CFC13 (1.5–2.0 ml) was added. H20 was added to the vial until full, then the vial was placed on a rotary shaker at 240 rpm for 20 minutes. The lower layer was withdrawn, and passed through a glass wool plugged pasteur pipette containing silica gel (0.3–0.4 g). The eluate was collected in Hewlett Packard autosampler vials and injected onto a 5890A chromatograph containing a 30 meter, 0.054" ID Megabore, 0.3 coated DB-1 column. The program parameters specified a hold period at 40° C. for 4 minutes, followed by a 10° C./minute temperature rise until 140 was attained.

The impact of the formulation on fluorochemical circulatory blood residence time is reported in Table IV.

TABLE IV
PERFLUOROCHEMICAL CIRCULATORY BLOOD RESIDENCE TIME

| Cpd | 48 hr Fct @ 20 cc |
|---|---|
| 1c | 6.18 |
| 1e | 6.72 |
| 1f | 8.18* |
| 1g | 7.22 |
| 1h | N/A |
| 1i | 4.93 |
| 1j | 8.65* |
| 1k | 5.38 |
| Control | 6.46 |

*significantly differs from control (Fisher Protected Least Significant Difference) at the 99% Confidence Level With reference to Table IV, it is apparent that emulsions made with the surfactants of this invention, especially as represented by compounds 1f and 1j, show increased stabilities in the circulatory blood system as measured by the amount of perfluorochemical remaining at 48 hours. Therefore, in addition to the stable PFC emulsions formed by the surfactants of this invention, they significantly increase the circulatory blood residence time of the PFC.

IMPACT OF FORMULATION ON ORGAN DISTRIBUTION OF PERFLUOROCHEMICAL

The impact of the emulsions of Table IV on organ distribution of PFC was then determined by sacrificing the test animals 14 days after infusion. The results of the organ analysis testing are shown in Table V.

TABLE V
ORGAN DISTRIBUTION 14 DAYS AFTER INFUSION OF 40 cc/Kg

| Cpd | Liver g/100 g | Spleen g/100 g | Lung g/100 g | Kidney g/100 g | Hct | Survival |
|---|---|---|---|---|---|---|
| 1e | 7.97 | 1.55** | 0.57* | 1.06 | 35.8 | 9/10 |
| 1g | 7.52* | 1.49** | 0.55* | 0.94 | 39.0* | 6/10 |
| 1i | 7.47* | 2.56 | 0.64* | 0.96 | 34.7 | 8/10 |
| 1j | 6.64** | 1.66** | 0.57** | 0.89 | 44.4** | 9/10 |
| 1k | 7.76* | 2.09* | 0.64* | 1.22 | 36.5 | 9/10 |
| Control | 9.13 | 2.89 | 0.87 | 1.02 | 31.7 | 9/10 |

*Significantly different from control at 99% confidence level by Fisher Protected Least Significant Difference
**Significantly different from control at 99% confidence level by Fisher Protected Least Significant Difference and by Scheffe F-test It is clear from Table V that the surfactant compounds of this invention greatly ameliorate the effects of perfluorochemical on the toxic responses of hepatomegaly, splenomegaly and lung enlargement. Furthermore, the surfactants do not cause nearly as large a drop in hematocrit (the v/v % of red blood cells—"Hct") after infusion. The result was so striking in the case of compound 1j that it was pursued in two additional separate studies as reported in Tables VI and VII.

TABLE VI
1-OCTADECYL-2-HEXADECYLGLYCERO-3-PHOSPHORYL CHOLINE SURFACTANT

| Cpd | Liver g/100 g | Spleen g/100 g | Lung g/100 g | Kidney g/100 g | Hct | Survival |
|---|---|---|---|---|---|---|
| 1j | 7.44 | 1.70* | 0.98 | 0.97 | 36.1 | 10/10 |
| Control | 7.99 | 2.51 | 0.92 | 0.93 | 32.1** | 8/10 |

*Significantly different from control at 97.4% probability by Student's t.
**Significantly different from control at 99.3% probability by Student's t.

TABLE VII

1-OCTADECYL-2-HEXADECYLGLYCERO-3-PHOSPHORYL CHOLINE SURFACTANT

| Cpd | Liver g/100 g | Spleen g/100 g | Lung g/100 g | Kidney g/100 g | Hct | Survival |
|---|---|---|---|---|---|---|
| 1j | 7.39 | 1.46* | 0.828 | 0.901 | 37.7* | 10/10 |
| Control | 7.82 | 2.78 | 0.838 | 0.943 | 34.1 | 10/10 |

*Significantly different from Control at 99% probability by Student's t.

Tables VI and VII demonstrate that splenomegaly was reduced and circulating red cell count as measured by hematocrit remained high. The effects on the liver and lung were not as pronounced in Table VI as in Table V. However, with respect to Table VII, it is believed that the smaller values obtained for the liver and spleen are also real. Even though the t-test does not show them to be significantly different in the individual studies at the 99% level, the liver weights remain smaller than the control, and the student t probability of a difference has been 86%. Accordingly, the odds of these results occurring in three separate experiments are very low. In addition, blood hematology was monitored by accredited outside laboratories and the results are shown in Table VIII.

TABLE VIII

BLOOD HEMOTOLOGY

| Cpd | RBC | Hemoglobin | Platelets | Reticulocytes |
|---|---|---|---|---|
| 1j | 5.42* | 11.04* | 1024222 | 313281** |
| Control | 4.80 | 9.79 | 920300 | 481858 |

*Significantly different from control at 99% probability by Student's t.
**Significantly different from control at 98% probability by Student's t.

With reference to Table VIII, these results demonstrate conclusively that increased circulating red cell count is real. With reference to the above detailed description and experimental results, the benefits of this invention may be appreciated. In summary, a new class of surfactants has been found to stabilize oil and water emulsions in a broad sense. The stability has been particularly demonstrated in the case of emulsions containing oils of triglycerides of fatty acids as emulsified particles and oleophilic perfluorochemicals as emulsified particles. In addition to the surprisingly stable PFC emulsions, the surfactants significantly increased the circulatory residence time of the PFC in animal blood, favorably altered the tissue distribution of the PFC in critical organs, and significantly ameliorated an adverse drop in red cell count.

The surfactants of this invention are also resistant to oxidation and degradation normally associated with egg yolk phospholipid lecithin emulsifying agents. Accordingly, emulsions containing the novel surfactants may be oxygenated during sterilization and through storage for extended periods without degradation due to these oxygen resistant surfactants.

In view of the above detailed description, other variations and embodiments of this invention will be understood to a person of ordinary skill in this art and such are within the scope and spirit of this description.

What is claimed is:

1. An emulsion comprising a fluorochemical, water and a surfactant having a general structure of

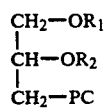

where $R_1$ and $R_2$ are a $C_{14}$–$C_{18}$ saturated or unsaturated aliphatic group and PC is the phosphoryl choline group or salt thereof represented by the structure

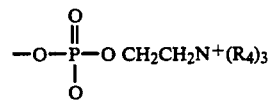

where $R_4$ is hydrogen or lower alkyl from the group consisting of methyl, ethyl and propyl.

2. The emulsion of claim 1 where $R_4$ is methyl.

3. The emulsion of claim 1 wherein said surfactant is selected from the group consisting of 1,2-ditetradecylglycero-3-phosphoryl choline, 1,2-dihexadecylglycero-3-phosphoryl choline, 1,2-dioctadecylglycero-3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1,2-octadecylglycero-3-phosphoryl choline, 1-octadecyl-2-hexadecylglycero-3-phosphoryl choline, 1-tetradecyl-2-hexadecylglycero-3-phosphoryl choline, and 1-hexadecyl-2-tetradecylglycero-3-phosphoryl choline.

4. The emulsion of claim 1 wherein the fluorochemical is selected from the group consisting of perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and mixtures thereof.

5. The emulsion of claim 4 that is stable after heat sterilization.

6. The emulsion of claim 1 wherein a liquid fatty oil is present as an emulsifying adjuvant in an amount between about 0.5 and about 30% by weight of the emulsion.

7. The emulsion of claim 6 wherein the oil is selected from the group consisting of mono-, di- and triglycerides, and mixtures thereof.

8. The emulsion of claim 1 wherein the surfactant is present in an amount of from about 0.5 to about 10% by weight of the emulsion.

9. The emulsion of claim 1 wherein the surfactant is present in an amount of from about 1 to about 2% by weight of the emulsion.

10. The emulsion of claim 1 wherein the fluorochemical is present in an amount of from about 10 to about 75% by volume of the emulsion.

11. The emulsion of claim 4 wherein said surfactant is selected from the group consisting of 1,2-ditetradecylglycero-3-phosphoryl choline, 1,2-dihexadecylglycero-3-phosphoryl choline, 1,2-dioctadecylglycero-3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3- phosphoryl choline, 1-hexadecyl-2-octadecylglycero-3-phosphoryl choline, 1,2-octadecylglycero-3-phosphoryl choline, 1-octadecyl-2-hexadecylglycero-3-phosphoryl choline, and 1-hexadecyl-2-tetradecylglycero-3-phosphoryl choline.

12. A physiologically acceptable emulsion comprising a fluorochemical, water and a surfactant having a general structure of

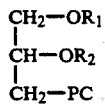

where $R_1$ and $R_2$ are a $C_{14}$–$C_{18}$ saturated or unsaturated aliphatic group and PC is the phosphoryl choline group or salt thereof represented by the structure

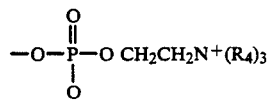

where $R_4$ is hydrogen or methyl.

13. The emulsion of claim 12 wherein said surfactant is selected from the group consisting of 1,2-ditetradecylglycero-3-phosphoryl choline, 1,2-dihexadecylglycero-3-phosphoryl choline, 1,2-di-octadecylglycero-3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1,2-dioctadecylglycero-3-phosphoryl choline, 1-octadecyl-2-hexadecylglycero-3-phosphoryl choline, 1-tetradecyl-2-hexadecylglycero-3-phosphoryl choline, and 1-hexadecyl-2-tetradecylglycero-3-phosphoryl choline.

14. The emulsion of claim 20 wherein said surfactant is contained in an amount of from about 0.5 to about 10% by weight of the emulsion.

15. The emulsion of claim 12 wherein a fluorochemical is contained in an amount of from about 10 to about 60% by volume of the emulsion.

16. The emulsion of claim 12 wherein said fluorochemical is contained in an amount of at least about 40% by volume of the emulsion.

17. The emulsion of claim 12 wherein said surfactant is 1-octadecyl-2-hexadecylglycero-3-phosphoryl choline.

* * * * *

UNITED STATES PATENT AND TRADEMARK OFFICE
CERTIFICATE OF CORRECTION

PATENT NO. : 5,304,325
DATED : April 19, 1994
INVENTOR(S) : Robert J. Kaufman and Thomas J. Richard It is certified that error appears in the above-indentified patent and that said Letters Patent is hereby corrected as shown below:

Col. 17, line 4, before "and", add -- 1-tetradecyl-2-hexadecylglycero-3-phosphoryl choline --.

Col. 18, line 14, "20" should be -- 12 --.

Signed and Sealed this

Fourth Day of October, 1994

Attest:

BRUCE LEHMAN

Attesting Officer                Commissioner of Patents and Trademarks